(12) United States Patent
Engelhardt et al.

(10) Patent No.: US 10,525,697 B2
(45) Date of Patent: Jan. 7, 2020

(54) INSPECTION SYSTEM HAVING A PLURALITY OF DETECTION ZONES

(71) Applicant: KOENIG & BAUER AG, Würzburg (DE)

(72) Inventors: David Engelhardt, Georgsmarienhütte (DE); Harald Willeke, Paderborn (DE)

(73) Assignee: Koenig & Bauer AG, Wurzburg (DE)

( * ) Notice: Subject to any disclaimer, the term of this patent is extended or adjusted under 35 U.S.C. 154(b) by 0 days.

(21) Appl. No.: 16/300,109

(22) PCT Filed: Jul. 10, 2017

(86) PCT No.: PCT/EP2017/067247
§ 371 (c)(1),
(2) Date: Nov. 9, 2018

(87) PCT Pub. No.: WO2018/015193
PCT Pub. Date: Jan. 25, 2018

(65) Prior Publication Data
US 2019/0176462 A1    Jun. 13, 2019

(30) Foreign Application Priority Data
Jul. 19, 2016  (DE) .......................... 10 2016 213 111

(51) Int. Cl.
*B41F 11/02*    (2006.01)
*G01N 21/86*    (2006.01)
(Continued)

(52) U.S. Cl.
CPC .......... *B41F 11/02* (2013.01); *B41F 33/0045* (2013.01); *B41F 33/0081* (2013.01);
(Continued)

(58) Field of Classification Search
None
See application file for complete search history.

(56) References Cited

U.S. PATENT DOCUMENTS 3,970,393 A    7/1976    Krygeris et al.
4,552,066 A *  11/1985    Giori .................. B41F 11/02
                                            101/152
(Continued)

FOREIGN PATENT DOCUMENTS

DE    102004014547 A1    12/2005
DE    102004061951 A1    7/2006
(Continued)

OTHER PUBLICATIONS

International Search Report of PCT/EP2017/067247 dated Oct. 20, 2017.

*Primary Examiner* — Jill E Culler
(74) *Attorney, Agent, or Firm* — Mattingly & Malur, PC

(57) ABSTRACT

An inspection system has a plurality of detection regions. The plurality of these detection regions of the inspection system are arranged to jointly inspect a printed sheet which has a plurality of printed regions. A first detection region is arranged to inspect a first printed region of the printed sheet and a second detection region is arranged to inspect a second printed region of the same printed sheet. A first measurement technology sensitivity is set for the first detection region and a second measurement technology sensitivity is set for the second detection region in the inspection system. The first measurement technology sensitivity and the second measurement technology sensitivity are set to be different from one another. The first measurement technology sensitivity and the second measurement technology sensitivity are set in each case either manually, by the use of an operating element, or automatically by the use of a program.

8 Claims, 2 Drawing Sheets

(51) Int. Cl.
  *B41F 33/00* (2006.01)
  *B42D 25/29* (2014.01)
  *B41M 3/14* (2006.01)
  *G01N 21/00* (2006.01)

(52) U.S. Cl.
  CPC .............. *B41M 3/14* (2013.01); *B42D 25/29* (2014.10); *B41F 33/0036* (2013.01); *G01N 21/00* (2013.01); *G01N 21/86* (2013.01)

(56) References Cited

U.S. PATENT DOCUMENTS

| | | | |
|---|---|---|---|
| 5,113,454 A * | 5/1992 | Marcantonio | G01N 21/86 |
| | | | 348/128 |
| 5,256,883 A * | 10/1993 | Weichmann | B41F 33/0036 |
| | | | 250/559.07 |
| 5,384,859 A * | 1/1995 | Bolza-Schunemann | B41F 33/0036 |
| | | | 347/19 |
| 5,767,980 A | 6/1998 | Wang et al. | |
| 5,912,988 A | 6/1999 | Moore | |
| 6,266,436 B1 * | 7/2001 | Bett | G06T 7/70 |
| | | | 382/111 |
| 6,772,689 B2 | 8/2004 | Endo et al. | |
| 7,027,934 B2 * | 4/2006 | Skeps | G01N 21/8901 |
| | | | 382/149 |
| 7,376,251 B2 * | 5/2008 | Stober | G01N 21/8903 |
| | | | 250/559.01 |
| 7,464,645 B2 | 12/2008 | Jeschonneck et al. | |
| 7,650,019 B2 | 1/2010 | Turke et al. | |
| 8,237,828 B2 | 8/2012 | Tatarczyk et al. | |
| 2002/0035939 A1 | 3/2002 | Endo et al. | |
| 2004/0008773 A1 * | 1/2004 | Itokawa | G01S 3/7864 |
| | | | 375/240.08 |
| 2004/0061325 A1 * | 4/2004 | Lyen | B41M 3/148 |
| | | | 283/72 |
| 2006/0239510 A1 | 10/2006 | Tatarczyk et al. | |
| 2007/0144375 A1 | 6/2007 | Jeschonneck et al. | |
| 2008/0212844 A1 | 9/2008 | Turke et al. | |
| 2009/0109430 A1 | 4/2009 | Stober | |

FOREIGN PATENT DOCUMENTS

| | | |
|---|---|---|
| DE | 102005018855 A1 | 11/2006 |
| DE | 102005031957 A1 | 1/2007 |
| DE | 102005054122 A1 | 5/2007 |
| EP | 0749833 A2 | 12/1996 |
| EP | 1190855 A1 | 3/2002 |
| EP | 1579992 A1 | 9/2005 |
| EP | 1714786 A2 | 10/2006 |
| EP | 1785276 A2 | 1/2013 |

* cited by examiner

INSPECTION SYSTEM HAVING A PLURALITY OF DETECTION ZONES

CROSS REFERENCE TO RELATED APPLICATIONS

This application is the U.S. National Phase, under 35 U.S.C. § 371, of PCT/EP2017/067247, filed Jul. 10, 2017; published as WO 2018/015193 A1 on Jan. 25, 2018, and claiming priority to DE 10 2016 213 111.7, filed Jul. 19, 2016, the disclosures of which are expressly incorporated in their enteritis herein by reference.

FIELD OF THE INVENTION

The present invention relates to an inspection system which has a plurality of detection zones, and to a method for adjusting the metrological sensitivity of an inspection system having a plurality of detection zones. The inspection system has a plurality of detection zones. The plurality of the detection zones of the inspection system are arranged for the joint inspection of a printed sheet containing a plurality of printed fields. A first detection zone is positioned for inspecting a first printed field of the printed sheet and a second detection zone is positioned for inspecting a second printed field of the same printed sheet. In the inspection system, a first metrological sensitivity is set for the first detection zone and a second metrological sensitivity is set for the second detection zone. The first metrological sensitivity and the second metrological sensitivity are set as different from one another. A plurality of these detection zones are used to jointly inspect a printed sheet having a plurality of fields to be printed. At least two of these fields of the printed sheet are printed prior to their inspection. A first detection zone of the inspection system is used to inspect a first printed field of the printed sheet and a second detection zone of the inspection system is used to inspect a second printed field of the same printed sheet.

BACKGROUND OF THE INVENTION

DE 10 2004 014 547 A1, DE 10 2005 031 957 A1, DE 10 2005 054 122 A1 and EP 1 190 855 A1 each disclose inspection systems for printing presses.

DE 10 2004 061 951 A1 discloses a system for controlling the quality of printed materials, in particular printed sheets, having a device for recording image data for the printed materials that are moved through a sheet-processing machine, for example a sheet-fed printing press, an analysis device downstream of the recording device for processing the image data in conjunction with data that are stored in a memory linked to the analysis device, wherein the recording device is capable of scanning printed material that reflects the fields to be inspected, and the analysis device is capable of determining therefrom the data that characterize the fields to be inspected or the image content thereof, storing these in the memory, and evaluating them during the subsequent analysis of image data for printed materials that are or will be processed, wherein it is provided that in the analysis device, using corresponding specifications regarding threshold values for brightness and/or color tone and/or saturation, those image regions that are a special color and are to be inspected are separated from image regions that will not be inspected.

EP 0 749 833 A2 discloses a video-based color sensor array for the control system of a printing press and a method for using the same, wherein for the joint inspection of a printed sheet, both a color camera for measuring in the visible range of the electromagnetic spectrum and a black and white camera for measuring in the non-visible infrared range are provided.

DE 10 2005 018 855 A1 discloses a device for inspecting, in particular, printed products produced by a printing press, in which a first camera, e.g. having a standard lens is provided, which is directed toward an inspection field on the printed product to be inspected, and at least one additional camera, e.g. having a telephoto lens is provided, which is directed at least partially toward the same inspection field already being monitored by the first camera, wherein the first camera captures an overview image of an inspection field, and the second camera captures a detail image of the inspection field with higher spatial resolution.

U.S. Pat. No. 5,912,988 A discloses a method for analyzing images, in which an overall image is divided into multiple individual fields, wherein each field can be evaluated individually.

In the production of printed products in a production system that has a printing press, it is customary for the printing properties of these printed products to be inspected in particular continuously, but at least sporadically, i.e. on a random basis, during the production process used to produce these printed products, in order to ensure the highest possible production quality. The properties of said printed product to be inspected that influence overall production quality include, e.g. the color density and/or the color value and/or the sharpness, in particular the edge sharpness of a printed image applied to a printing substrate. To carry out these inspections, inspection systems frequently are used which are preferably equipped with at least one optoelectronic camera, wherein said camera photographically images at least a portion of at least one printed image of the printed product in question, and from said imaging preferably generates digital image data of the image, which are then made available to an analysis unit, in particular an electronic analysis unit. The analysis unit analyzes the obtained image data with regard to the properties of said printed product to be inspected, and typically assesses the results of said inspection in that the analysis unit signals, dependent upon said inspection result, whether or not the inspected copy of the printed product meets the necessary requirements for production quality, e.g. established in advance by way of boundary values. Where necessary, when a production quality deficit is detected, the analysis unit transmits at least one signal, e.g. a control signal, to a unit of the production system or printing press involved in the production process, in order to correct this deficit in subsequently produced printed products and/or to channel defective printed products out of the production flow.

In security printing in particular, i.e. in the production of banknotes and other security documents, but also in the production, e.g. of high-quality packaging, a number of different printing methods are used in the production process. For example, an intaglio printing method and/or an offset printing method and/or a screen printing method and/or a plateless printing method, i.e. a digital printing method, e.g. an inkjet printing method and/or a laser printing method may be used in the production of banknotes. The various printing methods produce printed images that have different print properties, which is why, when performing an inspection of printed products having printed images produced by different methods, adjustments to the inspection system used for the inspection are necessary. A system is needed for the inspection of printed products produced in a production process using multiple different printing methods, which system is capable of examining at least one of the properties in or on each of the printed images of said printed product that have been printed by different printing methods.

SUMMARY OF THE INVENTION

The object of the invention is to devise an inspection system having a printing press that comprises an inspection system which has a plurality of detection zones and a method for adjusting the metrological sensitivity of an inspection system having a plurality of detection zones in which different detection zones are inspected using different sensitivities.

The object is attained according to the invention by the setting of each of the first metrological sensitivity and of the second metrological sensitivity either manually, by the use of a control element, or automatically by the use of a program. A first metrological sensitivity is set for the first detection zone and a second metrological sensitivity is set for the second detection zone. The first metrological sensitivity and the second metrological sensitivity are set such that they are different from each other.

The advantages to be achieved with the invention are, in particular, that different fields of a printed sheet on which printed images are formed, each in a different printing process, can each be inspected with a different sensitivity, resulting in a more accurate appraisal and a more balanced assessment of the quality of a printed product produced in a production system that includes a printing press, because, e.g. tolerances in the inspection system can be adjusted dependent upon the printing process that is used for each specific field. Furthermore, the proposed solution enables a statistical analysis of the ascertained quality of the printed product to be performed on a field-by-field basis, based upon the printing method used. The frequency of individual defects can be ascertained for the individual print fields that have been printed by different printing methods, and these frequencies can then form the basis for a more accurate control of the printing press.

BRIEF DESCRIPTION OF THE DRAWINGS

One exemplary embodiment of the invention is illustrated in the set of drawings and will be described in greater detail below.

In the drawings.

DESCRIPTION OF THE PREFERRED EMBODIMENT

Figure 1:
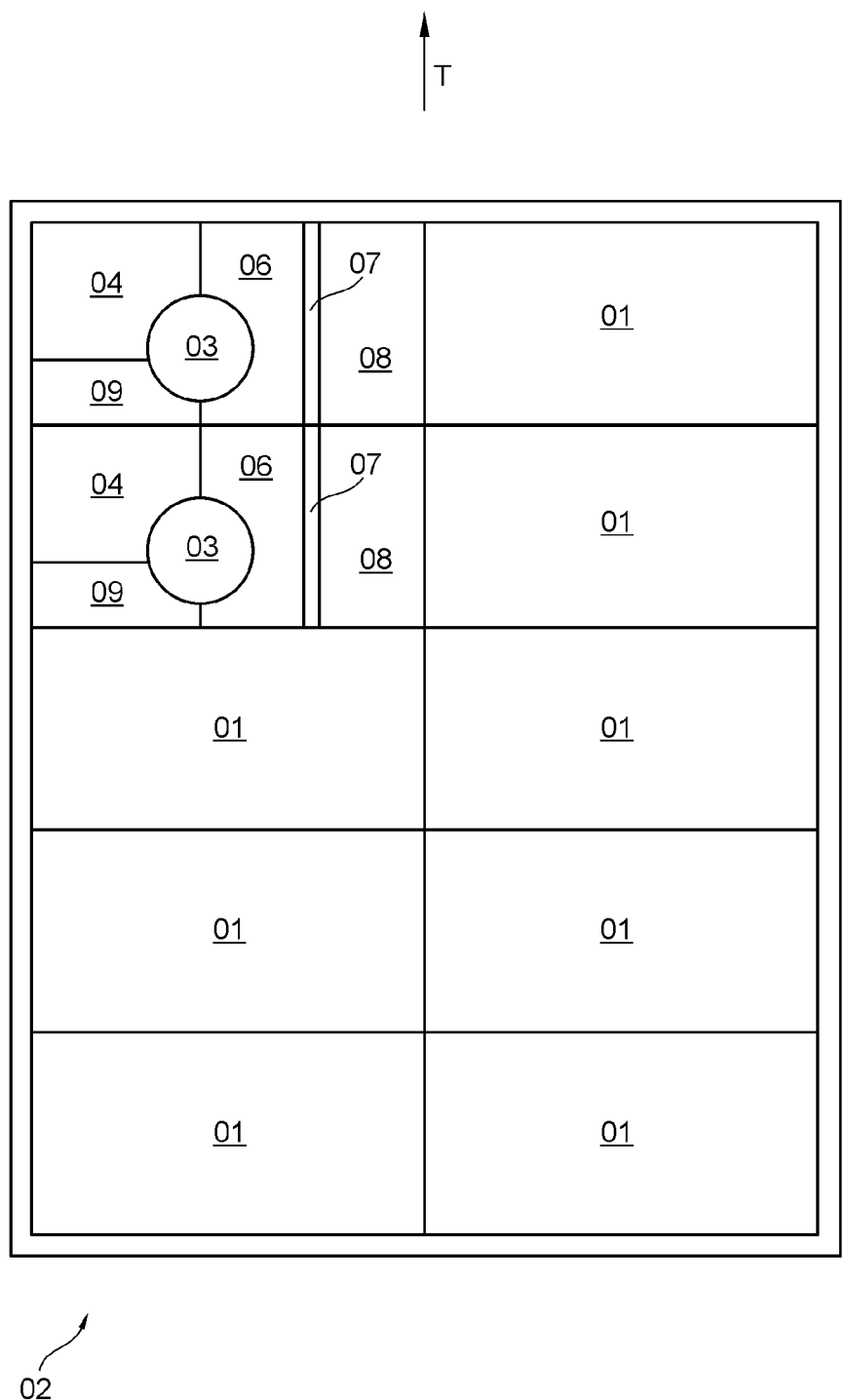
FIG. 1 shows a printed sheet containing a plurality of printed products, each having a plurality of fields that are or will be printed.

The exemplary embodiment is taken from the field of security printing and refers by way of example to the production of banknotes 01. Printed products, each formed or to be formed as a banknote 01, are produced on a printing substrate in a production system that includes at least one printing press, typically by a panel technique, in most cases with a printing substrate in the form of sheets 02, i.e. in each case a plurality of typically identical banknotes 01 are arranged, preferably in columns and rows, on each sheet 02 to be printed in a specific production process, as is shown by way of example in highly simplified form in FIG. 1. In the production of banknotes 01, usually a number of different printing methods are used, e.g. an intaglio printing method and/or an offset printing method and/or a screen printing method and/or a plateless printing method, i.e. a digital printing method, e.g. an inkjet printing method and/or a laser printing method. In most cases, in a given production process, a sequence comprising a plurality of these sheets 02 to be printed in this manner are guided, e.g. in a transport direction T indicated in FIG. 1 by a directional arrow, through the production system or the printing press, with each of these sheets 02 being printed on its transport route through said production system or printing press, typically one after the other, with different printing methods. Banknotes 01 of this type, typically in a rectangular format, accordingly each have a plurality of fields 03; 04; 06; 07; 08; 09 that have been or at least will be printed, wherein the print images to be located in at least two of said fields 03; 04; 06; 07; 08; 09 will be or are produced on said sheet 02, in particular composed of paper, by the use of different printing methods. Different fields 03; 04; 06; 07; 08; 09 of a banknote 01 produced in this manner differ from one another, e.g. in that in a field 03 containing a printed image produced by an intaglio printing method, the printed image is configured, e.g. as more intricate or having sharper contours than a printed image in a field 04; 06; 07; 08; 09 containing a printed image produced, e.g. by an offset printing method or by a screen printing method.

To ensure the highest possible production quality, it is provided for at least some of the print images printed in a particular production process to be inspected, by means of an inspection system, with regard to certain properties relating to printing technology that influence the quality of the printed product in question, e.g. color density and/or color value and/or sharpness, in particular the edge sharpness of the printed images in question. Sharpness refers to the distinctness of details in a printed image and as a numerical measure of sharpness, e.g. the set of mutually distinguishable lines is determined. The more abrupt the transition from dark to light is in a photographic image of a printed image, the higher the edge sharpness is. For a balanced assessment of the quality produced, it is advantageous for the printed images that are produced in different fields 03; 04; 06; 07; 08; 09 of the printed product in question using different printing methods to be inspected using different sensitivity levels, meaning that a different metrological sensitivity is set in the inspection system for each of the different fields 03; 04; 06; 07; 08; 09 of the printed product to be inspected. In metrology, the term "sensitivity" is defined according to DIN 1319 as the "change in the value of the output variable of a measuring instrument based upon the change in the value of the input variable that causes it". Metrological sensitivity thus describes the relationship between a variable to be measured, e.g. color density or color value or sharpness, and a measurement signal that corresponds to the respective variable to be measured, e.g. an electrical voltage, in particular a measured value, e.g. displayed on a scale. A measurement method is considered to be sensitive if a small change in the variable to be measured produces a large change in the measurement signal.

Figure 2:
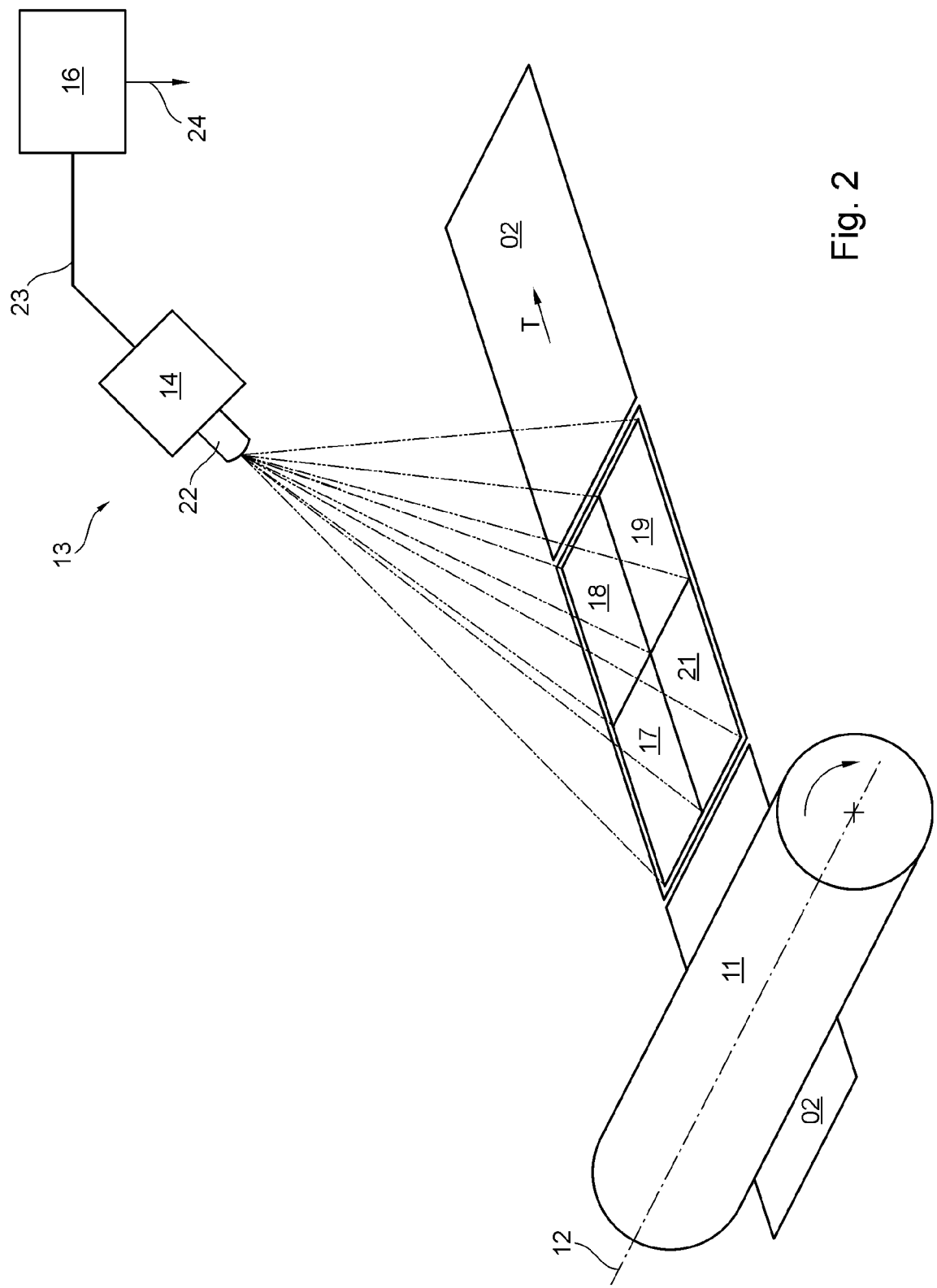
FIG. 2 shows an inspection system having a plurality of detection zones.

FIG. 2 is a highly simplified diagram of a sequence of a plurality of sheets 02 being guided in succession through a production system that includes a printing press and printed therein by means of at least one printing couple, with the at least one printing couple indicated by way of example in FIG. 2 including, e.g. at least one printing cylinder 11, each such cylinder rotating about a rotational axis 12. At least one of the printing couples preferably applies at least one print image to each of the sheets 02, e.g. in an intaglio printing method. In addition, at least one additional print image is applied to each of the sheets 02, guided in succession along the transport path through the production system, by means of a different printing method, e.g. by an offset printing method and/or by a screen printing method and/or by a plateless printing method. At the end of the transport path of the sheets 02 being guided through the production system, an inspection system 13 is preferably located, preferably having at least one camera 14; the at least one camera 14 forwards its respective preferably digital image data to an analysis unit 16, in particular an electronic analysis unit, for analyzing and evaluating said image data. The inspection system 13, in particular the at least one camera 14 thereof, is configured as having a plurality of detection zones 17; 18; 19; 21, the sensitivity of which can preferably be adjusted independently of one another.

In one preferred embodiment, this means that an inspection system 13 in a production system that is equipped with a printing press, or an inspection system disposed in or on a measuring table is preferably configured in either case to photographically image a printed sheet 02 or an individual printed product, e.g. a banknote 01, in full, but at least to photographically image a portion of a printed image. For this purpose, the inspection system 13 is equipped with a plurality of detection zones 17; 18; 19; 21, with a plurality of these detection zones 17; 18; 19; 21 of the inspection system 13 each being arranged for the joint inspection of a printed sheet 02 containing a plurality of printed fields 03; 04; 06; 07; 08; 09. The joint, e.g. also simultaneous inspection of a plurality of printed fields 03; 04; 06; 07; 08; 09 of a printed sheet 02 is enabled by a corresponding arrangement and/or configuration of the detection zones 17; 18; 19; 21 of the inspection system 13, in which, e.g. appropriate lenses 22 or other optical systems are used in conjunction with the at least one camera 14 of the inspection system 13. Each at least one camera 14 of the inspection system 13 is preferably configured as an optoelectronic camera 14, with each said camera 14 preferably generating digital image data in the photographic imaging of the at least one printed image. These image data are made available via a wired or wireless data link 23 to an analysis unit 16, in particular an electronic analysis unit. The analysis unit 16 then analyzes the image data generated from the detection of said printed sheet 02 or said at least one printed image and obtained from at least two different detection zones 17; 18; 19; 21, the metrological sensitivities of which are set as different from one another, with regard to the properties to be inspected of the printed product in question, and generally rates the inspection result in that the analysis unit 16 signals, based upon the inspection result in each case, whether or not the inspected copy of the printed product meets the requirements for production quality, e.g. established in advance by way of boundary values, in each of the detection zones 17; 18; 19; 21. Where necessary, when a production quality deficit is detected the analysis unit 16 transmits at least one signal 24, e.g. a control signal, to a unit of the production system or printing press involved in the production process, e.g. to an inking unit and/or dampening unit and/or to a register controlling device, in particular to a color register controlling device, in order to correct this deficit in subsequently produced printed products and/or to channel defective printed products out of the production flow. The inspection performed by the inspection system 13 of printed products printed in a given production process is carried out, in particular continuously, but at least sporadically, i.e. on a random basis.

According to the invention, in the inspection system 13 in question, a first detection zone 17 is positioned for inspecting a first printed field of printed sheet 02 and a second detection zone 18 is positioned for inspecting a second printed field of the same printed sheet 02, wherein in the inspection system 13, a first metrological sensitivity is set for the first detection zone 17 and a second metrological sensitivity is set for the second detection zone 18, the first metrological sensitivity and the second metrological sensitivity being set as different from one another. In one preferred embodiment, the metrological sensitivity of the first detection zone 17 for inspecting the first printed field of printed sheet 02 is set as higher than the metrological sensitivity of the second detection zone 18 for inspecting the second printed field of printed sheet 02. The first metrological sensitivity and the second metrological sensitivity are each set manually by means of a control element or automatically by means of a program.

In the inspection system 13 which has, e.g. the above-described plurality of detection zones 17; 18; 19; 21, a method for adjusting the metrological sensitivity can be carried out, in which a printed sheet 02 having a plurality of fields to be printed is inspected with a plurality of these detection zones 17; 18; 19; 21 jointly, in which case at least two of these fields of the printed sheet 02 are printed prior to their inspection. In one preferred embodiment, the first field to be inspected on the printed sheet 02 is printed by an intaglio printing method, and the second field to be inspected on the printed sheet 02 is printed by an offset printing method or by a screen printing method or by a plateless printing method. A first printed field of the printed sheet 02 is inspected with a first detection zone 17 of the inspection system 13, and a second printed field of the same printed sheet 02 is inspected with a second detection zone 18 of said inspection system 13. According to the invention, a first metrological sensitivity is set in or on the inspection system 13 for the first detection zone 17, and a second metrological sensitivity is set for the second detection zone 18, wherein the first metrological sensitivity and the second metrological sensitivity are set such that they are different from one another.

In a particularly advantageous refinement of the proposed method, during a setup phase of the production system or the printing press or the measuring table, a prepress sheet, which is different from a production sheet used for producing a finished product, is used as sheet 02, in which the field of the prepress sheet that is printed by the intaglio printing method is detected by one of the detection zones 17 of inspection system 13, and this detection zone 17 in inspection system 13 is specified as the first detection zone 17 thereof for the inspection of at least one first field, printed by the intaglio printing method, on a production sheet that will be used subsequently in the production of the finished product. In this process, the field of the prepress sheet printed by the intaglio printing method during the setup phase of the production system or the printing press or the measuring table is preferably printed without wiping. Wiping is performed, e.g. by means of a doctor blade and a wiping cylinder. Printing without wiping means that the gravure in the intaglio plate remains filled with printing ink, and excess printing ink is not removed. In addition, typically no fields of the prepress sheet are printed by an offset printing method or by any printing method other than the intaglio printing method. It may be provided that in the first field of the printed sheet 02 in question, printed by the intaglio printing method, at least the contours of at least one part of the field may be blurred, e.g. due to excess printing ink. In that case, after being detected, e.g. by means of at least one imaging operation used in the inspection system 13, the at least one blurred contour is formed as a sharp contour, in which case the imaging operation consists, e.g. in a morphological function. For example, the imaging operation consists in the performance of binarization and/or closing and/or dilation and/or erosion. Binarization also enables, e.g. printed fields of the printed sheet 02 in question to be separated from unprinted fields thereof in the photographic image. An unprinted field of the printed sheet 02 shows, e.g. only the white paper thereof.

While a preferred embodiment of an inspection system having a plurality of inspection zones, in accordance with the present invention, has been set forth fully and completely hereinabove, it will be apparent that various changes could be made thereto, without departing from the true spirit and scope of the present invention, which is accordingly to be limited only by the appended claims.

The invention claimed is:

1. A production system having comprising:
a printing press that includes an inspection system, which inspection system has a plurality of detection zones, wherein the plurality of detection zones of the inspection system are arranged for the joint inspection of a printed sheet containing a plurality of printed fields, wherein a first one of the plurality of detection zone zones is positioned for inspecting a first printed field of the printed sheet and wherein a second one of the plurality of detection zones is positioned for inspecting a second printed field of the same printed sheet, wherein, in the inspection system, a first metrological sensitivity is set for the first detection zone and a second metrological sensitivity is set for the second detection zone, wherein the first metrological sensitivity and the second metrological sensitivity are different from one another, wherein the first metrological sensitivity and the second metrological sensitivity are each set one of manually by a control element and automatically by a program, wherein the printing press of the production system comprises a plurality of printing couples, wherein at least two of these printing couples are arranged to print onto the same printing sheet, wherein one of these at least two printing couples for printing onto the same printing sheet is embodied as a printing couple for printing the printing sheet in an intaglio printing process and wherein another printing couple of the at least two printing couples is embodied as a printing couple for printing the printing sheet in one of an offset printing process and in a screen printing process and in a plateless printing process, wherein a field, printed in the intaglio printing process, and without wiping, and of a prepress sheet used during a setup phase of the printing press, is detected by one of the plurality of detection zones of the inspection system and is specified, in the inspection system, as the first detection zone thereof for the inspection of at least one first field printed by the intaglio printing method on a production sheet that will be used subsequently in the production of the finished product.

2. The production system according to claim 1, wherein the metrological sensitivity of the first detection zone for inspecting the first printed field of the printed sheet is higher than the metrological sensitivity of the second detection zone for inspecting the second printed field of the printed sheet.

3. The production system according to claim 1, wherein a camera for detecting the printed sheet is provided, wherein the camera is connected to an analysis unit, wherein the camera forwards digital image data generated from the detection of the printed sheet to the analysis unit, wherein the analysis unit analyzes and evaluates these image data in at least two different detection zones, the metrological sensitivities of which at least two different detection zones are different from one another.

4. The production system according to claim 1, wherein each of the first and second metrological sensitivity is formed as a relationship between a variable to be measured and a measurement signal that corresponds to the variable to be measured, wherein the variable to be measured is one of a color density and a color value and a sharpness, and wherein the measurement signal that corresponds to the variable to be measured is one of a measured value and an electrical voltage displayed on a scale.

5. The production system according to claim 1, wherein the inspection system is located at an end of a transport path of the printed sheet which is guided through the production system.

6. A method for adjusting the metrological sensitivity of an inspection system having a plurality of detection zones, wherein the method is implemented in a production system having one of a printing press and a measuring table, in which a printed sheet, having a plurality of fields to be printed, is inspected using the plurality of detection zones jointly, in which at least two of the plurality of fields of the printed sheet to be detected are printed prior to their inspection, in which a first detection zone of the plurality of detection zones of the inspection system is used to inspect a first printed field of the printed sheet and in which a second detection zone of the plurality of detection zones of the inspection system is used to inspect a second printed field of the same printed sheet, in which, one of in and on the inspection system, a first metrological sensitivity is set for the first detection zone and a second metrological sensitivity is set for the second detection zone, wherein the first metrological sensitivity and the second metrological sensitivity are different from one another, wherein the first metrological sensitivity and the second metrological sensitivity are each set one of manually, by a control element, and automatically, by a program, in which, during a setup phase of the one of the production system and the measuring table, a prepress sheet, which is different from a production sheet used for the production of a finished product, is used as the printed sheet, wherein the first field to be inspected on the printed sheet is printed by an intaglio printing method and wherein the second field to be inspected on the printed sheet is printed by one of an offset printing method and a screen printing method and a plateless printing method, wherein the field of the prepress sheet, printed by the intaglio printing method during the setup phase of the production system, is printed without wiping, in which the field of the prepress sheet printed by the intaglio printing method, without wiping, is detected by one of the plurality of detection zones of the inspection system and this one detection zone of the plurality of detection zones is specified in the inspection system as the first detection zone thereof for the inspection of at least one first field printed by the intaglio printing method on a production sheet that will be used subsequently, in the production of a finished product.

7. The method according to claim 6, wherein, in the first field of the printed prepress sheet, printed by the intaglio printing method, at least the contours of at least one portion of the field may be blurred.

8. The method according to claim 7, wherein, once it has been detected, the at least one portion of the field which may be blurred, that portion of the field is formed as a sharp contour by using at least one imaging operation used in the inspection system.

* * * * *